(12) United States Patent
Gyory

(10) Patent No.: US 11,642,459 B2
(45) Date of Patent: May 9, 2023

(54) SYSTEM AND METHOD FOR AIR REMOVAL

(71) Applicant: Becton, Dickinson and Company, Franklin Lakes, NJ (US)

(72) Inventor: J. Richard Gyory, Sudbury, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 329 days.

(21) Appl. No.: 16/743,751

(22) Filed: Jan. 15, 2020

(65) Prior Publication Data

US 2021/0213198 A1   Jul. 15, 2021

(51) Int. Cl.
*A61M 5/168* (2006.01)
*A61M 5/142* (2006.01)
*A61M 5/14* (2006.01)

(52) U.S. Cl.
CPC .... *A61M 5/16822* (2013.01); *A61M 5/14248* (2013.01); *A61M 5/16809* (2013.01); *A61M 2005/1402* (2013.01); *A61M 2205/3337* (2013.01); *A61M 2205/3344* (2013.01); *A61M 2205/3389* (2013.01); *A61M 2205/7536* (2013.01)

(58) Field of Classification Search
CPC .......... A61M 5/14248; A61M 5/16822; A61M 5/36; A61M 5/38; A61M 5/385
See application file for complete search history.

(56) References Cited

U.S. PATENT DOCUMENTS

| 7,517,387 | B2 * | 4/2009 | Chevallet | A61M 1/3641 604/122 |
| 8,480,609 | B2 * | 7/2013 | Fava | A61M 1/1694 604/5.04 |
| 8,728,020 | B2 * | 5/2014 | Caleffi | A61M 5/16854 604/5.01 |
| 2008/0119822 | A1 * | 5/2008 | Knauper | A61J 15/0076 604/151 |
| 2009/0309465 | A1 | 12/2009 | Quirico et al. | |
| 2010/0280434 | A1 | 4/2010 | Raney et al. | |
| 2011/0040229 | A1 | 2/2011 | Hannan et al. | |
| 2012/0226235 | A1 * | 9/2012 | Larsen | A61M 5/36 604/123 |
| 2016/0220753 | A1 | 8/2016 | Ambrosina et al. | |
| 2016/0346485 | A1 | 12/2016 | Mohr et al. | |
| 2018/0272058 | A1 | 9/2018 | Pizzochero et al. | |
| 2019/0009023 | A1 * | 1/2019 | Diperna | A61M 5/14248 |
| 2019/0240424 | A1 | 8/2019 | Rudolph et al. | |

FOREIGN PATENT DOCUMENTS

WO    WO-2009147478 A1 *  12/2009  ............ A61M 1/342

* cited by examiner

*Primary Examiner* — Laura A Bouchelle
(74) *Attorney, Agent, or Firm* — Dickinson Wright PLLC

(57) ABSTRACT

A system and method removing air from a reservoir, the system comprising the reservoir that carries a medicament, a first pump connected to the reservoir that draws the medicament out of the reservoir, an air removal device connected to the first pump that releases air from the medicament, and a second pump connected to the air removal device that delivers the medicament.

19 Claims, 7 Drawing Sheets

SYSTEM AND METHOD FOR AIR REMOVAL

FIELD OF THE INVENTION

The present invention relates to an air removal system that removes air from a medicament in a medical device.

BACKGROUND OF THE INVENTION

Diabetes is a group of diseases characterized by high levels of blood glucose resulting from the inability of diabetic patients to maintain proper levels of insulin production when required. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient. Type 1 diabetes (T1D) patients are required to take insulin (e.g., via injections or infusion) to move glucose from the bloodstream because their bodies generally cannot produce insulin. Type 2 diabetes (T2D) patients generally can produce insulin but their bodies cannot use the insulin properly to maintain blood glucose levels within medically acceptable ranges. In contrast to people with T1D, the majority of those with T2D usually do not require daily doses of insulin to survive. Many people are able to manage their condition through a healthy diet and increased physical activity or oral medication. However, if they are unable to regulate their blood glucose levels, they will be prescribed insulin. For example, there are an estimated 6.2 million Type 2 diabetes patients (e.g., in the United States, Western Europe and Canada) taking multiple-daily-injections (MDI) which consist of a 24-hour basal insulin and a short acting rapid insulin that is taken at mealtimes for glycemic management control.

For the treatment of Type 1 diabetes (T1D) and sometimes Type 2 diabetes (T2D), there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates to more closely match the functions and behavior of a properly operating pancreas of a non-diabetic person that produces the required insulin, and the insulin pump can help the diabetic patient maintain his/her blood glucose level within target ranges based on the diabetic patient's individual needs. Infusion pump therapy requires an infusion cannula, typically in the form of an infusion needle or a flexible catheter, that pierces the diabetic patient's skin and through which infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life. For example, many of the T2D patients who are prescribed insulin therapy can be expected to convert from injections to infusion therapy due to an unmet clinical need for improved control. That is, a significant number of the T2D patients who take multiple-daily-injections (MDI) are not achieving target glucose control or not adhering sufficiently to their prescribed insulin therapy.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps use a disposable component, typically referred to as an infusion set, tubing set or pump set, which conveys the insulin from a reservoir within the pump into the skin of the user. The infusion set includes a pump connector, a length of tubing, and a hub or base from which a cannula, in the form of a hollow metal infusion needle or flexible plastic catheter, extends. The base typically has an adhesive that retains the base on the skin surface during use. The cannula can be inserted onto the skin manually or with the aid of a manual or automatic insertion device. The insertion device may be a separate unit employed by the user.

Another type of insulin pump is a patch pump. Unlike a conventional infusion pump and infusion set combination, a patch pump is an integrated device that combines most or all of the fluidic components in a single housing. Generally, the housing is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such patch pumps are replaced on a frequent basis, such as every three days, or when the insulin reservoir is exhausted. Otherwise, complications may occur, such as restriction in the cannula or the infusion site.

As a patch pump is designed to be a self-contained unit that is worn by the patient, preferably, the patch pump is small, so that it does not interfere with the activities of the user. In current patch pump designs, tubes, such as plastic tubes, are employed as fluid pathways to route fluid flow from one internal component to another. For example, a tube can connect a medicament reservoir with a delivery needle. Typically, medicament is drawn from the medicament reservoir via a vacuum. However, in such a configuration, it is very difficult to remove entrapped air from the medicament. This is because the vacuum draws the medicament via a negative pressure with respect to atmospheric pressure. Medicament at a negative pressure will draw in air instead of releasing air. Accordingly, a need exists for an improved system and method to remove air from the medicament prior to medicament delivery.

SUMMARY OF EMBODIMENTS OF THE INVENTION

It is an aspect of the present invention to provide a system that draws medicament into a system having a positive pressure with respect to the atmospheric pressure. The positive pressure of the system allows the air to naturally exit the medicament, thus improving dose accuracy.

The foregoing and/or other aspects of the present invention can be achieved by providing a system for removing air from a reservoir, the system comprising the reservoir that carries a medicament, a first pump connected to the reservoir that draws the medicament out of the reservoir, an air removal device connected to the first pump that releases air from the medicament, and a second pump connected to the air removal device that delivers the medicament.

The foregoing and/or other aspects of the present invention can also be achieved by providing a device for delivering medicament into skin of a patient, the device comprising a housing and a base enclosing a reservoir that carries a medicament, a first pump connected to the reservoir that draws the medicament out of the reservoir, an air removal device connected to the first pump that releases air from the medicament, and a second pump connected to the air removal device that delivers the medicament, wherein the base is configured to be attached to the skin of a patient.

The foregoing and/or other aspects of the present invention can be further achieved by providing a method of removing air from a medicament prior to medicament delivery, the method comprising drawing medicament from a reservoir, routing the medicament through a system, releasing air from the medicament, and delivering the medicament at a predetermined pressure.

Additional and/or other aspects and advantages of the present invention will be set forth in the description that follows, or will be apparent from the description, or may be learned by practice of the invention. The present invention may comprise delivery devices and methods for forming and operating the same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and/or other aspects and advantages of embodiments of the invention will be more readily appreciated from the following detailed description, taken in conjunction with the accompanying drawings, of which.

DETAILED DESCRIPTION OF EMBODIMENTS OF THE PRESENT INVENTION

Figure 1:
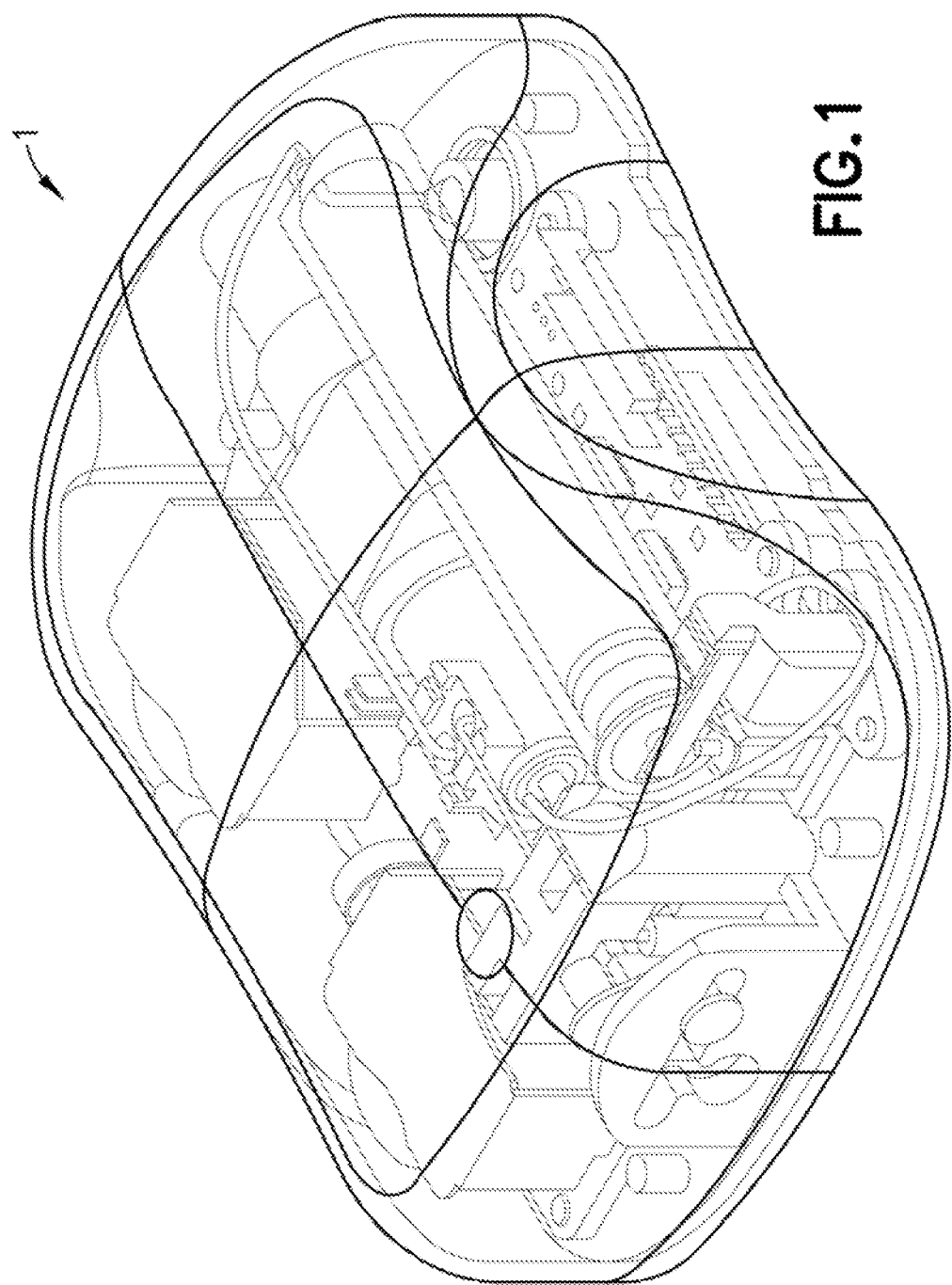
FIG. 1 is a perspective view of a patch pump constructed in accordance with an illustrative embodiment of the present invention.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The inventions described herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The illustrative embodiments are described with reference to diabetes management using insulin therapy. However, it is to be understood that these illustrative embodiments can be used with different drug therapies and regimens to treat other physiological conditions other than diabetes using medicaments other than insulin.

Figure 2:
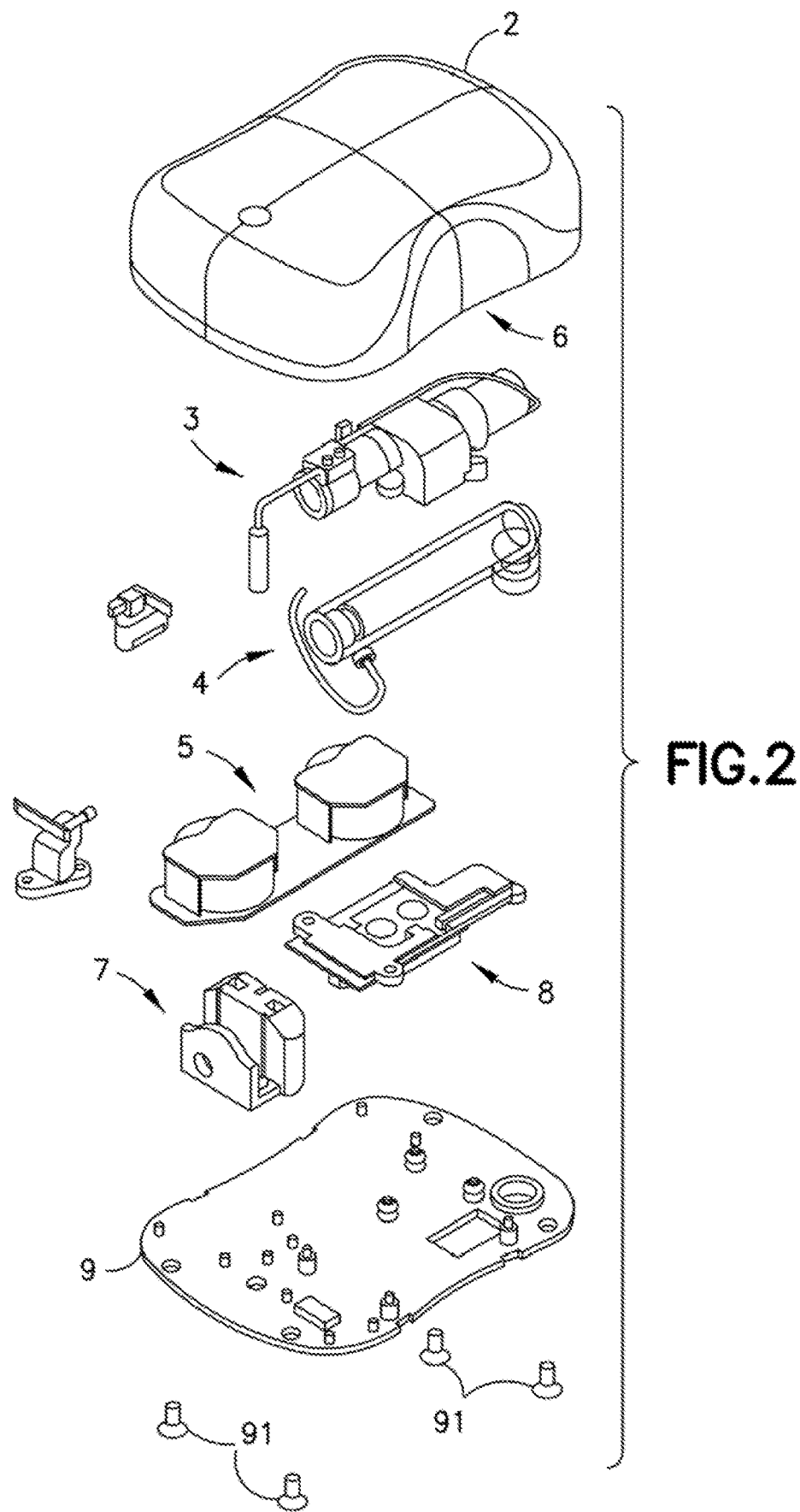
FIG. 2 is an exploded view of the various components of the patch pump of FIG. 1, illustrated with a cover.

FIG. 1 is a perspective view of an exemplary embodiment of a medicament delivery device comprising a patch pump 1 according to an exemplary embodiment of the invention. The patch pump 1 is illustrated with a see-through cover for clarity and illustrates various components that are assembled to form the patch pump 1. FIG. 2 is an exploded view of the various components of the patch pump of FIG. 1, illustrated with a main cover 2. The various components of the patch pump 1 may include: a reservoir 4 for storing insulin or other liquid medicament; a pump 3 for pumping insulin out of the reservoir 4; a power source 5 in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a pair of dose buttons 6 on the cover 2 for actuating an insulin dose, including a basal and/or bolus dose; and a base 9 to which various components above may be attached via fasteners 91. The patch pump 1 also includes various fluid connector lines that transfer insulin pumped out of the reservoir 4 to the infusion site.

Figure 3:
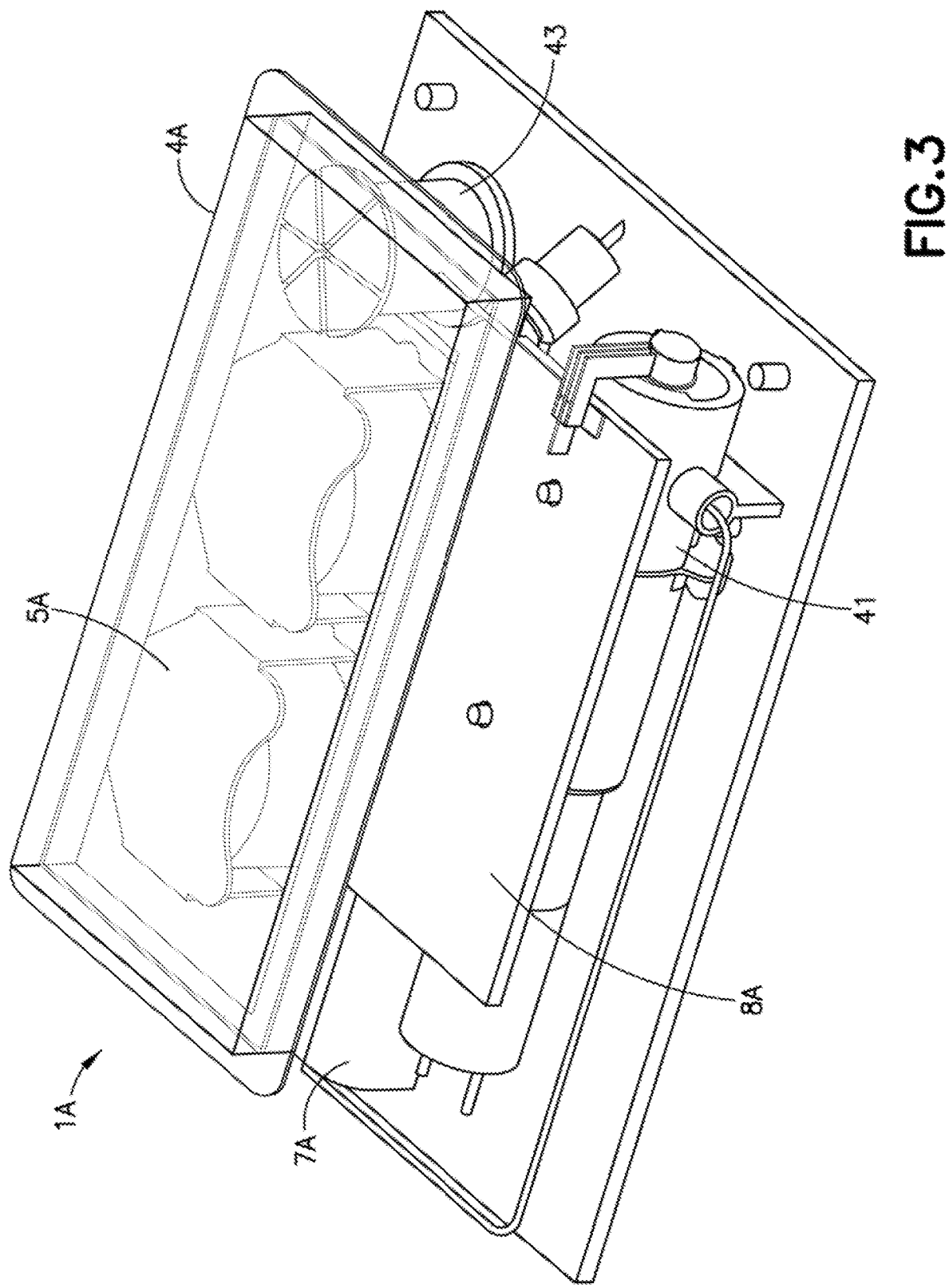
FIG. 3 is a perspective view of an alternative design for a patch pump having a flexible reservoir, illustrated without a cover, in accordance with an illustrative embodiment of the present invention.

FIG. 3 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe to fill the reservoir 4A.

Figure 4:
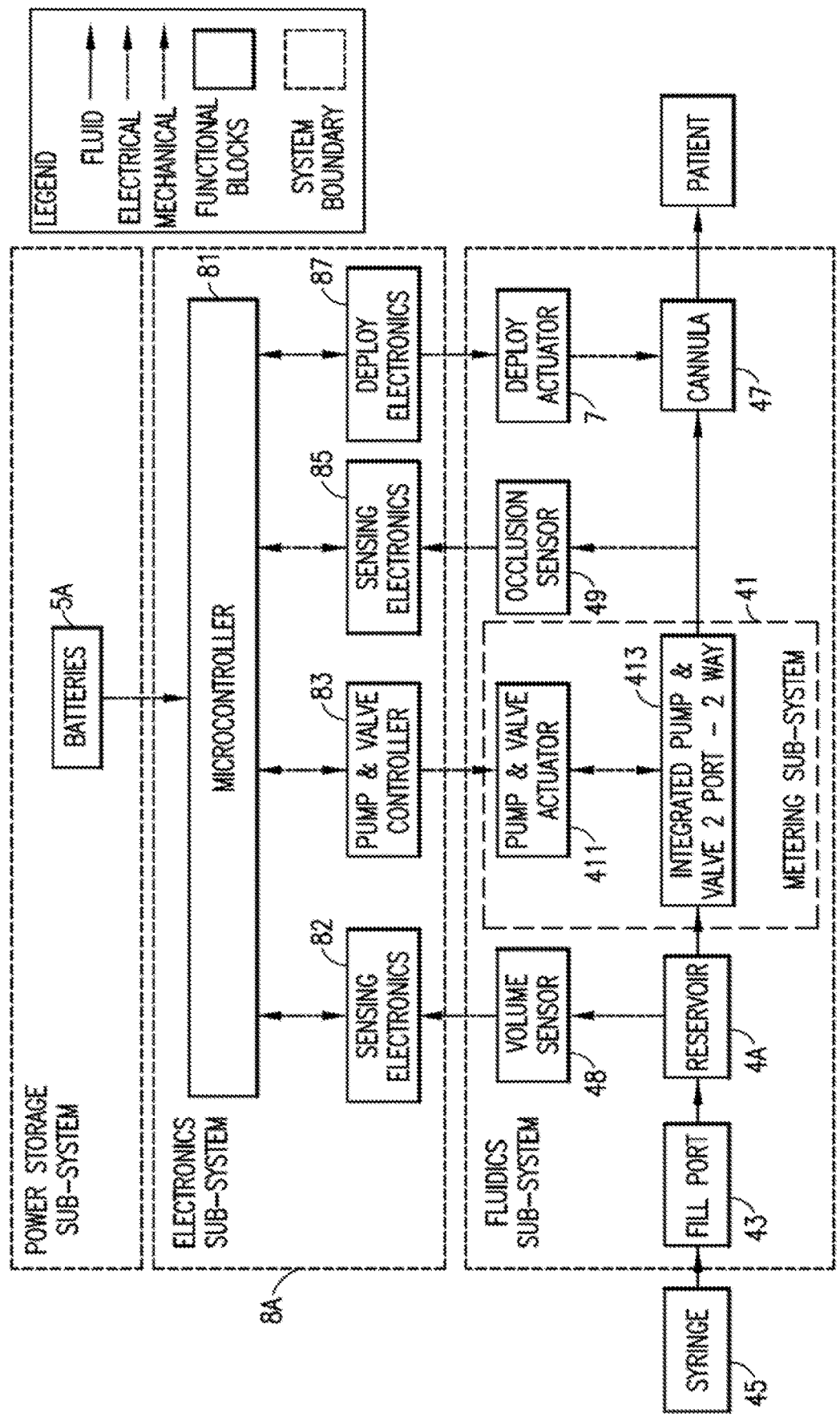
FIG. 4 is a perspective view of a fluidic architecture and metering sub-system diagram of the patch pump of FIG. 3.

FIG. 4 is a fluidic architecture and metering sub-system diagram for the patch pump 1A of FIG. 3. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87, which control the actuation of the patch pump 1A. The patch pump 1A includes a fluidics sub-system that may include a reservoir 4A, volume sensor 48 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 1 and 2 can be the same or similar to that which is illustrated in FIG. 4.

Figure 5:
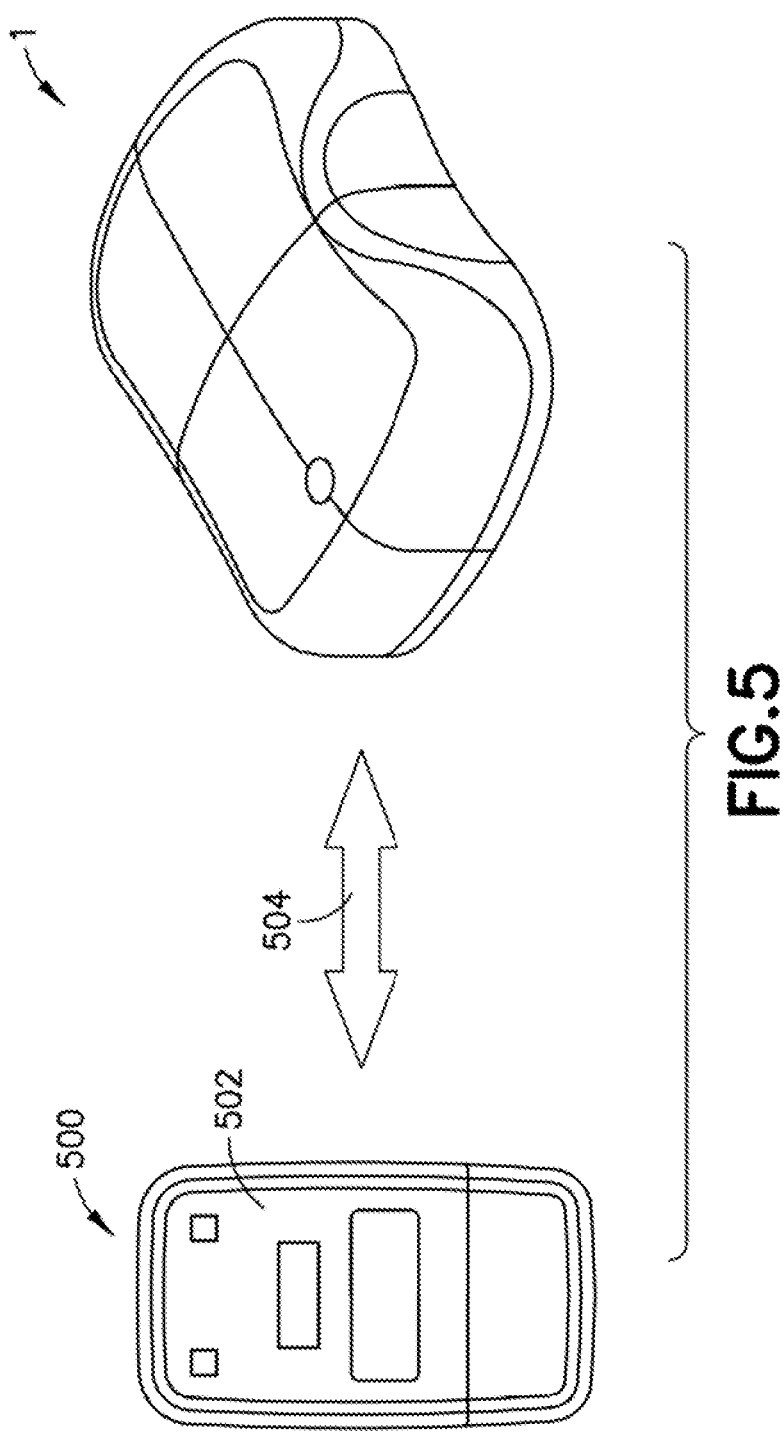
FIG. 5 illustrates a wireless remote controller for controlling the operation of a medicine delivery device such as, for example, a patch pump, in accordance with an illustrative embodiment of the present invention.

With reference to FIG. 5, the wearable medical delivery device (e.g., insulin delivery device (IDD) such as patch pump 1 or 1A) is operable in conjunction with a remote controller that preferably communicates wirelessly with the pump 1 or 1A and is hereinafter referred to as the wireless controller (WC) 500. The WC can comprise a graphical user interface (GUI) display 502 for providing a user visual information about the operation of the patch pump 1 or 1A such as, for example, configuration settings, an indication when a wireless connection to the patch pump is successful, and a visual indication when a dose is being delivered, among other display operations. The GUI display 502 can include a touchscreen display that is programmed to allow a user to provide touch inputs such as a swipe to unlock, swipe to confirm a request to deliver a bolus, and selection of confirmation or settings buttons, among other user interface operations.

The WC 500 can communicate with the delivery device (e.g., patch pump 1 or 1A) using any one or more of a number of communication interfaces 504. For example, a near field radiation interface is provided to synchronize the timing of the WC and patch pump 1 or 1A to facilitate pairing upon start up. Another interface can be provided for wireless communication between the WC and the patch pump 1 or 1A that employs a standard BlueTooth Low Energy (BLE) layer, as well as Transport and Application layers. Non-limiting examples of Application layer commands include priming, delivering basal dose, delivering bolus dose, cancelling insulin delivery, checking patch pump 1 or 1A status, deactivating the patch pump 1 or 1A, and patch pump 1 or 1A status or information reply.

Figure 6:
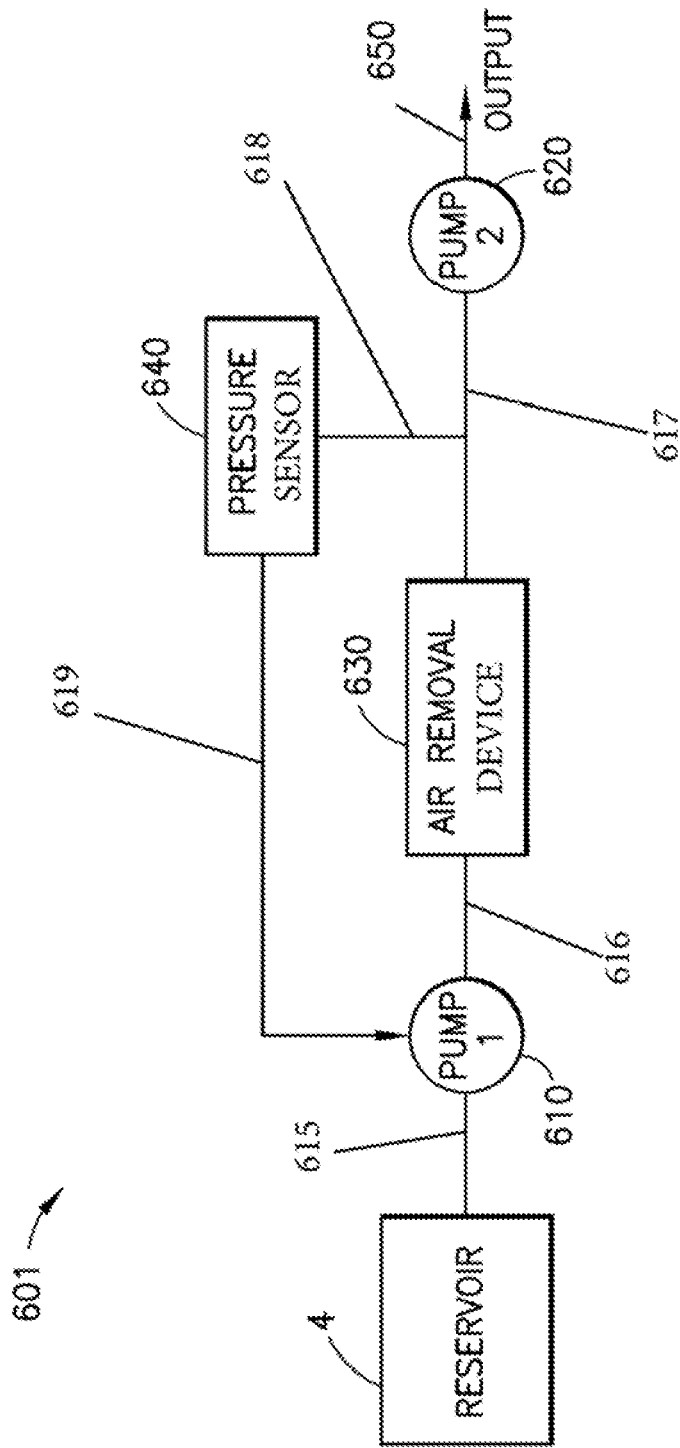
FIG. 6 is a schematic diagram of an air removal system for a patch pump in accordance with an illustrative embodiment of the present invention.

FIG. 6 is a perspective view of an air removal system 601 in the patch pump 1 or 1A according to an exemplary embodiment of the present invention. The air removal system 601 includes a first pump 610, a second pump 620, an air removal device 630, a pressure sensor 640, and an output 650. These elements are connected via medicament lines 615-618 and electrical line 619 as described below.

The first pump 610 is connected to the reservoir 4 and draws or extracts the medicament from the reservoir 4 through medicament line 615. The first pump 610 does not return medicament to the reservoir 4 through medicament line 615. The first pump 610 is a typical vacuum-based pump that creates negative pressure in its chamber to remove the medicament from the reservoir 4. As described above, the reservoir 4 can be a flexible reservoir that expands and contracts based on transfer of the medicament. The reservoir can also be a rigid reservoir as traditionally known and used. A rigid reservoir provides a fixed volume to carry the medicament.

The air removal device 630 preferably comprises a hydrophobic membrane that advantageously allows air to escape but prevents liquid from escaping. One exemplary membrane is a Durapore Microfiltration Superhydrophobic Membrane manufactured by Millipore Corporation (Catalog No. SVSP50205). The Millipore SVSP membrane is made of a modified polyvinylidene fluoride on a nonwoven polyester support with a pore size of 5.0 µm, a thickness of 160 µm and an air flow rate greater than 1.3 slpm/cm$^2$ at 1 psi. Another exemplary membrane is a Fluoropore Membrane manufactured by Millipore Corporation (Catalog No. FGLP29325). The Millipore FGLP membrane is made of Hydrophobic Polytetrafloroethylene (PTFE) with a pore size of 0.22 µm, a thickness of 175 µm and an air flow rate of 3 L/min×cm$^2$. Further exemplary membranes include a hydrophobic polycarbonate membrane manufactured by Sterlitech Corporation, and hydrophobic and oleophobic membranes manufactured by W.L. Gore & Associates, Inc. An exemplary porous membrane is also disclosed and illustrated by Xu et al. in "Use of a Porous Membrane for Gas Bubbles Removal in Microfluidic Channels: Physical Mechanisms and Design Criteria," published online on Mar. 24, 2010 by Springer-Verlag and incorporated herein by reference for this purpose (see https://www.me.iastate.edu/files/2011/09/bubble_removal_microfl_nanofl.pdf).

The air removal device 630 does not allow medicament to travel through the membrane. Rather, the medicament travels along the air removal device 630 so that air can escape. Specifically, high surface tension fluids, such as water, are prevented from entering the pore structure of the hydrophobic membrane. When air contacts the hydrophobic membrane, the air is allowed to pass through the hydrophobic membrane thereby eliminating the air from the retained aqueous solution.

The air removal device 630 can also be implemented as a filter, separator, etc. The air removal device 630 is downstream of the first pump 610 and medicament line 615 and in fluid communication with the first pump 610 via medicament line 616.

The air removal device 630 removes air from the medicament that is drawn from the reservoir 4. Specifically, as more medicament is removed from the reservoir 4 by the first pump 610, the medicament routed into the medicament lines 616 and 617 increases in positive pressure. When the pressure of the medicament in the medicament lines 616 and 617 is greater than atmospheric pressure, the air from the medicament will exit through the air removal device 630. At the same time, the air removal device 630 prevents the medicament from exiting the air removal system 601.

The pressure sensor 640 is downstream of the air removal device 630 and is connected to medicament line 617 by a tap line 618. Thus, the medicament lines 616 and 617 are closed and pressure-controlled based on the operation of the first and second pumps 610, 620. The pressure sensor 640 also advantageously communicates with the first pump 610 via a microcontroller (not shown) and the electrical control line 619 to regulate the pressure of the medicament. Specifically, the first pump 610 draws medicament from the reservoir 4, through medicament line 615 and into the medicament line 616. As the first pump 610 draws more and more medicament into the medicament line 616, the pressure of the medicament in the medicament lines 616 and 617 increases and air is able to escape via the air removal device 630.

The air removal device 630 fluidly communicates between the first pump 610 and the pressure sensor 640. Such a configuration advantageously allows the pressure sensor 640 to accurately monitor the pressure of the medicament in the medicament lines 616 and 617 while the device 630 removes the excess air in the medicament.

The medicament in the medicament lines 616 and 617 travels downstream to the second pump 620 to ultimately administer the medicament to the patient. When the medicament reaches the second pump 620, the medicament is at a predetermined pressure. The predetermined pressure is an elevated pressure that is greater than the atmospheric pressure. The first pump 610 advantageously drives the medicament at a faster rate than the second pump 620. In this manner, the medicament lines 616 and 617 are pressurized and the second pump 620 receives pressurized medicament in order to satisfy medicament delivery requirements. The second pump 620 advantageously operates independently from the first pump 610 and from the pressure sensor 640.

The air removal device 630 and the pressure sensor 640 are fluidly disposed between the first and second pumps 610, 620. This configuration advantageously allows air in the medicament to be released before the medicament arrives at the second pump 620. Also, a specific pressure can be advantageously regulated in the medicament lines 616 and 617 prior to the second pump 620 driving the medicament.

Upon achieving the elevated pressure, the second pump 620 routes and transfers the medicament to an outlet 650 of the air removal system 601. In this manner, the second pump 620 regulates the pressure and amount of medicament that exits the output 650 of the air removal system 601 and through the patch pump 1 or 1A, for example.

The pressure sensor 640 senses and regulates pressure of the medicament in the medicament lines 616 and 617. Specifically, the pressure sensor 640 communicates with the first pump 610 to pump the medicament into the medicament lines 616 and 617. The second pump 620 advantageously operates independently from the first pump 610 and the pressure sensor 640. From the second pump 620, the medicament exits the air removal system 601 at the output 650, travels to various parts of the patch pump 1 or 1A, for example, and is ultimately administered to a patient.

The medicament at the elevated pressure advantageously allows the second pump 620 to operate and control the delivery of the medicament at a desired rate without a danger of having air in the medicament line 615. Removal of the air from the medicament avoids dose accuracy problems. Even if the reservoir 4 contains air and medicament, the air removal system 601 maintains dose accuracy because the air is removed at the air removal device 630 prior to exiting the air removal system 601. Accordingly, patient care and clinician experience are improved.

Figure 7:
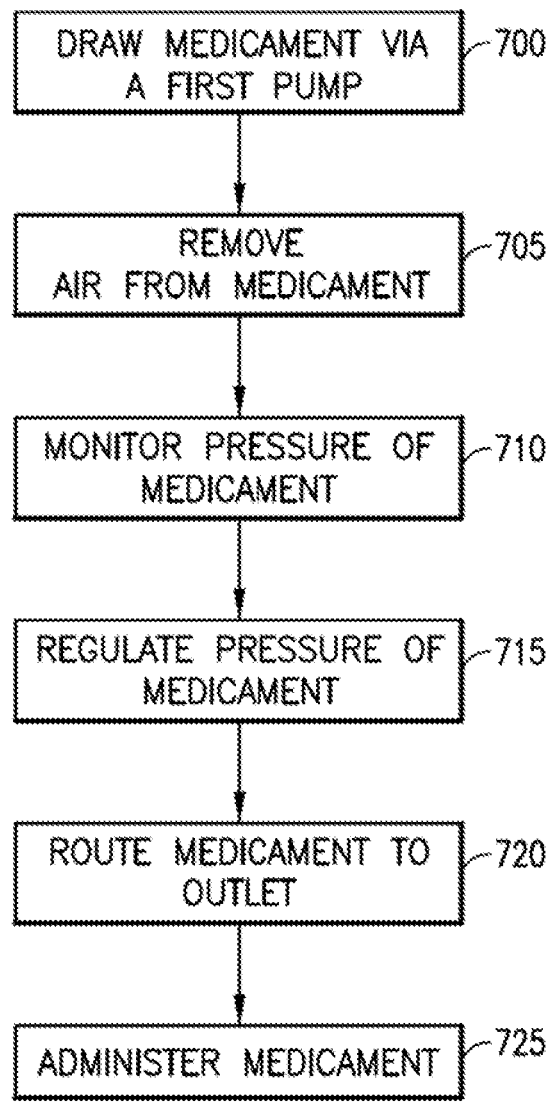
FIG. 7 is a flow diagram of the operation of the air removal system of FIG. 6.

FIGS. 6 and 7 illustrates the operation of the air removal system 601. In step 700, the first pump 610 draws the medicament from the reservoir 4 into the medicament line 615. The first pump 610 draws the medicament via a vacuum (negative pressure) into its chamber and supplies the medicament into the medicament lines 616 and 617 at a positive (greater than atmospheric) pressure. Also, the first pump 610 does not allow medicament to return to the reservoir 4 through the first pump 610 via the medicament line 615. The pressure sensor 640 ensures that a positive pressure is maintained in the medicament lines 616, 617. This positive pressure in the medicament lines 616, 617 then "pushes" any air out of the system through the air removal membrane 630 while the hydrophobic nature of the air removal membrane 630 retains the aqueous medicament fluid.

As more medicament is drawn into the medicament lines 616 and 617, the pressure of the medicament increases to a pressure greater than atmospheric pressure. According to step 705, when the pressure of the medicament in the medicament lines 616 and 617 is greater than atmospheric pressure, air in the medicament is advantageously released through the air removal device 630.

The pressure of the medicament in the medicament lines 616 and 617 will fluctuate. This is because the air in the medicament is removed by the air removal device 630. Additionally, more medicament may be entering into the medicament lines 616 and 617. Thus, in accordance with step 710, the pressure of the medicament is monitored by the pressure sensor 640 through this process.

According to step 715, in addition to monitoring the pressure of the medicament, the pressure sensor 640 advantageously cooperates with the first pump 610 to regulate the pressure and the amount of the medicament in the medicament lines 616 and 617. Specifically, the pressure sensor 640 achieves a predetermined pressure of the medicament in the medicament lines 616 and 617 by instructing the first pump 610 to provide the appropriate amount of medicament. The pressure sensor 640 dynamically controls the pressure of the medicament because any given quantity of medicament that enters into the medicament lines 616 and 617 can have a different amount of air.

In step 720, the second pump 620 receives the pressurized medicament and is able to route and transfer the pressurized medicament to exit the air removal system 601 through the output 650. The second pump 620 regulates the pressure and amount of medicament that exits the output 650 and through the patch pump 1 or 1A, for example. The first pump 610 advantageously drives the medicament at a faster rate than the second pump 620 so that the second pump 620 can receive pressurized medicament and satisfy delivery requirements.

In step 725, the medicament travels to various parts of the patch pump 1 or 1A and is ultimately administered to a patient. The second pump 620 is able to operate and control the delivery of the medicament at a desired rate and pressure to meet delivery requirements and without danger of having air in the medicament at the output 650. As a result, dose accuracy, patient care and clinician experience are all improved.

Although only a few embodiments of the present invention have been shown and described, the present invention is not limited to the described embodiments. Instead, it will be appreciated by those skilled in the art that changes may be made to these embodiments without departing from the principles and spirit of the invention. It is particularly noted that those skilled in the art can readily combine the various technical aspects and elements of the various exemplary embodiments that have been described above in numerous other ways, all of which are considered to be within the scope of the invention, which is defined by the appended claims and their equivalents.

What is claimed is:

1. A system for removing air from a reservoir, the system comprising:
   the reservoir that carries a medicament;
   a first pump connected to the reservoir that draws the medicament out of the reservoir;
   an air removal device connected to the first pump that releases air from the medicament;
   a pressure sensor connected to the air removal device via a medicament line, the pressure sensor monitors pressure of the medicament, the pressure sensor ensures that a positive pressure is maintained in the medicament lines upstream and downstream from the air removal device; and
   a second pump connected to the air removal device that delivers the medicament; wherein
   the pressure sensor is disposed downstream from the air removal device;
   the second pump is disposed downstream from the pressure sensor; and
   the pressure sensor communicates with the first pump to regulate the pressure of the medicament.

2. The system according to claim 1, wherein the reservoir comprises a rigid reservoir.

3. The system according to claim 1, wherein the reservoir comprises a flexible reservoir.

4. The system according to claim 1, wherein the air removal device comprises a hydrophobic membrane.

5. The system according to claim 1, wherein the pressure sensor communicates with the first pump to regulate the pressure of the medicament by pumping the medicament into the medicament line upstream and downstream from the air removal device.

6. The system according to claim 1, wherein the pressure sensor does not electrically communicate with the second pump.

7. The system according to claim 1, wherein the air removal device fluidly communicates between the first pump and the pressure sensor.

8. The system according to claim 1, wherein
   the pressure sensor is in fluid communication with the first pump and the second pump; and
   a valve is absent from the system.

9. The system according to claim 1, wherein
   the first pump drives the medicament at a faster rate than the second pump; and
   the first pump does not return the medicament to the reservoir.

10. The system according to claim 1, wherein the second pump does not electrically communicate with the first pump.

11. The system according to claim 1, wherein the air removal device releases the air from the medicament when a pressure of the medicament is at a predetermined value.

12. The system according to claim 11, wherein the predetermined value is greater than atmospheric pressure.

13. A device for delivering medicament into skin of a patient, the device comprising:
    a housing and a base enclosing:
       a reservoir that carries a medicament;
       a first pump connected to the reservoir that draws the medicament out of the reservoir;
       an air removal device connected to the first pump that releases air from the medicament;
       a pressure sensor that ensures a positive pressure is maintained in medicament lines upstream and downstream from the air removal device; and
       a second pump connected to the air removal device that delivers the medicament; wherein
    the base is configured to be attached to the skin of a patient.

14. The device of claim 13, wherein the housing and the base further enclosing:
    a fill port in fluid communication with the second pump;
    a delivery mechanism in communication with the fill port that delivers the medicament into skin of a patient; and
    a valve is absent from the device.

15. A method of removing air from a medicament prior to medicament delivery, the method comprising:
    drawing medicament from a reservoir via a first pump;
    routing the medicament through a system;
    releasing air, via an air removal device, from the medicament;
    monitoring pressure, via a pressure sensor, of the air in the medicament using a fluid line to establish fluid communication between the pressure sensor and the air removal device, the pressure sensor being disposed downstream from the air removal device; and
    delivering the medicament via a second pump; wherein
    the pressure sensor ensures that a positive pressure is maintained in the medicament lines upstream and downstream from the air removal device;
    the second pump is disposed downstream from the pressure sensor; and
    the pressure sensor communicates with the first pump to regulate the pressure of the medicament.

16. The method according to claim 15, further comprising regulating the pressure of the medicament in the system.

17. The method according to claim 16, further comprising drawing medicament based on the pressure of the medicament drawn into the system.

18. The method according to claim 15, further comprising delivering the medicament at the pressure equal to or greater than a predetermined value.

19. The method according to claim 15, further comprising delivering the medicament at a slower rate than drawing the medicament.

* * * * *